United States Patent
Lassner et al.

(10) Patent No.: US 6,686,515 B1
(45) Date of Patent: Feb. 3, 2004

(54) HOMOLOGOUS RECOMBINATION IN PLANTS

(75) Inventors: Michael Lassner, Davis, CA (US); Steven delCardayre, Belmont, CA (US)

(73) Assignee: Maxygen, Inc., Redwood City, CA (US)

(*) Notice: Subject to any disclaimer, the term of this patent is extended or adjusted under 35 U.S.C. 154(b) by 74 days.

(21) Appl. No.: 09/721,582

(22) Filed: Nov. 22, 2000

Related U.S. Application Data

(60) Provisional application No. 60/167,450, filed on Nov. 23, 1999.

(51) Int. Cl.[7] .......................... A01H 1/00; C12N 15/82; C12N 15/00; C12Q 1/68; C12Q 19/34; C07H 21/04

(52) U.S. Cl. .......................... 800/294; 435/6; 435/91.2; 435/440; 536/23.1; 536/24.3; 536/24.33; 536/6

(58) Field of Search ...................... 800/294; 435/6, 435/91.2, 440; 536/23.1, 24.3, 24.33

(56) References Cited

U.S. PATENT DOCUMENTS

| | | |
|---|---|---|
| 5,512,463 A | 4/1996 | Stemmer |
| 5,514,588 A | 5/1996 | Varadaraj |
| 5,605,793 A | 2/1997 | Stemmer |
| 5,763,239 A | 6/1998 | Short et al. |
| 5,789,228 A | 8/1998 | Lam et al. |
| 5,811,238 A | 9/1998 | Stemmer et al. |
| 5,814,473 A | 9/1998 | Warren et al. |
| 5,824,469 A | 10/1998 | Horwitz et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minushull et al. |
| 5,866,363 A | 2/1999 | Pieczenik |
| 5,876,997 A | 3/1999 | Kretz |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,985,646 A | 11/1999 | Murphy et al. |
| 6,001,574 A | 12/1999 | Short et al. |
| 6,004,788 A | 12/1999 | Short |
| 6,030,779 A | 2/2000 | Short |
| 6,054,267 A | 4/2000 | Short |
| 6,096,548 A | 8/2000 | Stemmer |
| 6,117,679 A | 9/2000 | Stemmer |
| 6,132,970 A | 10/2000 | Stemmer |

FOREIGN PATENT DOCUMENTS

| | | |
|---|---|---|
| EP | 0911396 A2 | 4/1999 |
| EP | 0911396 A3 | 5/1999 |
| EP | 0934999 A1 | 8/1999 |
| WO | WO 93/22443 A1 | 11/1993 |
| WO | WO 97/07205 | 2/1997 |
| WO | WO 97/08331 A1 | 3/1997 |
| WO | WO 97/20078 | 6/1997 |
| WO | WO 97/25410 | 7/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | * 7/1998 |
| WO | WO 98/36080 | 8/1998 |

(List continued on next page.)

OTHER PUBLICATIONS

Citovsky et al. Nuclear Localization of Agrobacterium VirE2 Protein in Plant cells. Science. vol. 256, pp. 1802–1805, Jun. 1992.*

Ogawa et al. (1992) "Functional Structures of the RecA Protein Found by Chimera Analysis." *J. Mol. Biol.* 226:651–660.

Brendel et al. (1997) "Evolutionary Comparisons of RecA–Like Proteing Across All Major Kingdoms of Living Organisms." *J. Mol. Biol.* 44:528–541.

Citovsky et al. (1992) "Nuclear Localization of Agrobacterium VirE2 Protein in Plant Cells." *Science* 256:1802–1805.

Shcherbakova et al. (2000) "Overexpression of bacterial RecA protein stimulates homologous recombination in somatic mammalian cells." *Mutation Research* 65–71.

(List continued on next page.)

*Primary Examiner*—Kenneth R. Horlick
*Assistant Examiner*—Cynthia Wilder
(74) *Attorney, Agent, or Firm*—Joanne R. Petithory; Christopher Holman; Norman J. Kruse

(57) ABSTRACT

Methods for evolving recombinase protein homologues and RecA/VirE2 fusion proteins which complement VirE2 deficient Agrobacterium are provided. The use of recombinase protein homologues and RecA/VirE2 fusion proteins in the context of Agrobacterium mediated transformation are provided. Methods for producing transgenic organisms by homologous recombination using evolved recombinase proteins and Agrobacterium strains which express recombinase protein homologues or RecA/VirE2 fusion proteins are provided. Transgenic cells and organisms which have integrated an exogenous DNA sequence into a predetermined site in their genome are provided.

12 Claims, No Drawings

FOREIGN PATENT DOCUMENTS

| | | |
|---|---|---|
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |
| WO | WO 00/42560 | 7/2000 |
| WO | WO 00/42561 | 7/2000 |
| WO | WO 00/53744 | 9/2000 |
| WO | WO 00/58517 | 10/2000 |

OTHER PUBLICATIONS

Ziemienowicz et al. (2001) "Import of Agrobacterium T–DNA into Plant Nuclei: Two Distinct Functions of VirD2 and VirE2 Proteins." *The Plant Cell* 13:369–383.

Chang, C., et al. (1999) "Evolution of a cytokine using DNA family shuffling." *Nature Biotechnology* 17:793–797.

Christians, F.C. et al., (1999) "Directed evolution of thymidine kinase for AZT phosphorylation using DNA family shuffling." *Nature Biotechnology* 17:259–264.

Crameri et al., (1993) "10(20)–Fold aptamer library amplification without gel purification," *Nuc. Acids Res.* 21(18):4410.

Crameri, A. & Stemmer W.P.C. (1995) "Combinatorial multiple cassette mutagenesis creates all the permutations of mutant and wildtype cassettes." *Biotechniques* 18:194–195.

Crameri, A. et al. (1996) "Improved green fluorescent protein by molecular evolution using DNA shuffling." *Nature Biotechnology* 14:315–319.

Crameri, A. et al. (1996) "Construction and evolution of antibody–phage libraries by DNA shuffling." *Nature Medicine* 2:100–103.

Crameri, A. et al., (1997) "Molecular evolution of an arsenate detoxification pathway by DNA shuffling." *Nature Biotechnology* 15:436–438.

Crameri, A. et al., (1998) "DNA shuffling of a family of genes from diverse species accelerates directed evolution." *Nature* 391:288–291.

Gates, C.M. et al., (1996) "Affinity selective isolation of ligands from peptide libraries through display on a lac repressor headpiece dimer". *Journal of Molecular Biology* 255:373–386.

Minshull, J., Stemmer, W.P.C. (1999) "Protein evolution by molecular breeding." *Current Opinion in Chemical Biology* 3:284–290.

Ness, J. et al., (1999) "DNA shuffling of subgenominc sequences of subtilisin." *Nature Biotechnology* 17:893–896.

Patten, P.A. et al., (1997) "Application of DNA Shuffling to Pharmaceuticals and Vaccines." *Current Opinion in Biotechnology* 8:724–733.

Stemmer, W.P.C. (1994) "DNA Shuffling by random fragmentation and reassembly: In vitro recombination for molecular evolution." *PNAS* 91:10751.

Stemmer, W.P.C. (1994) "Rapid evolution of a protein in vitro by DNA shuffling." *Nature* 370:389–391.

Stemmer, W.P.C. (1995) "The Evolution of Molecular Computation." *Science* 270:1510.

Stemmer, W.P.C. (1995) "Searching Sequence Space." *Bio/Technology* 13:549–553.

Stemmer, W.P.C. (1996) "Sexual PCR and Assembly PCR." In: *The Encyclopedia of Molecular Biology*. VCH Publishers, New York. pp. 447–457.

Stemmer, W.P.C. & Soong, N.W. (1999) "Molecular breeding of viruses for targeting and other clinical properties." *Tumor Targeting* 4:59–62.

Zhang, J. et al., (1997) "Directed evolution of an effective fucosidase from a galactosidase by DNA shuffling and screening." *Proceedings of the National Academy of Sciences, USA* 94:4504–4509.

* cited by examiner

HOMOLOGOUS RECOMBINATION IN PLANTS

COPYRIGHT NOTIFICATION PURSUANT TO 37 C.F.R. § 1.71(E)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCE TO RELATED APPLICATIONS

This application claims priority to and benefit of U.S. application Ser. No. 60/167,450, filed Nov. 23, 1999, which is incorporated in its entirety for all purposes.

BACKGROUND OF THE INVENTION

The production of genetically altered plant species is of major agricultural and economic importance. In recent years, methods based on recombinant DNA techniques have led to the introduction of exogenous DNA from a variety of sources into the genomes of plant cells and explants. Regeneration of these genetically altered cells or explants into transgenic plants has dramatically increased the potential for discrete modifications of commercially relevant plant phenotypes.

A number of techniques exist for introducing exogenous DNA into plant cells, such as protoplasts, which are capable of subsequent regeneration, such as, microinjection of naked DNA, electroporation, Ca/PEG precipitation, and particle bombardment-mediated delivery, so called "biolistics." Alternatively, it is possible to take advantage of the natural DNA transfer system of Agrobacterium to transfer exogenous DNA to plant chromosomes.

Agrobacterium mediated transformation relies on the ability of *A. tumefaciens* or *A. rhizogenes* to transfer DNA molecules called T-DNA to a host plant cell. *A. tumefaciens* and *A. rhizogenes* are the causative agents of the plant neoplastic diseases crown gall and hairy root disease, respectively. Agrobacteria, which reside normally in the soil, detect soluble molecules secreted by wounded plant tissues through a specialized signal detection/transformtion system. In the presence of these chemical signals, agrobacteria attach to the cell walls of wound exposed plant tissues. The agrobacteria then excise and transfer a portion of specialized DNA, designated T-DNA and delimited by T-DNA borders, to the host plant cell nucleus where it is integrated into the chromosomal DNA.

This DNA transfer system can be manipulated to transfer exogenous DNA situated between T-DNA borders to a host plant cell of choice. While Agrobacterium are typically restricted to infecting dicotyledonous species under natural conditions, by manipulating the conditions of infection, efficient transformation of monocots, including some crop species has been possible.

Common to the methods specified above is the integration of the exogenous DNA to a random site in the plant chromosome. While useful for many applications, random integration of transgenes leaves a number of difficulties. For example, the targeted disruption of an endogenous gene requires that integration occur at a specified locus in the host plant genome. Similarly, the ability to delete an endogenous gene and replace it with one that has been improved or modified, is of great commercial interest. In addition, great variability in expression levels exists between random integration events. The capacity to target insertion to a specific promoter or chromatin region conferring a desirable level or pattern of expression is a significant benefit that is gained by inserting a transgene at a predetermined site in the recipient genome.

Techniques available for directing transgenes to predetermined sites in the genomes of multicellular eukaryotes rely, on one hand, on homologous recombination between a transgene and an insertion site with which the transgene shares regions of sequence similarity; and on the other hand, on site specific recombinases. In the first case, large regions of sequence similarity flank a DNA sequence which introduces an alteration, most frequently a disruption, into a gene of interest. In the case of site specific recombinases, most commonly the Cre recombinase of bacteriophage P1 or the *Saccharomyces cerevisiae* FLP recombinase, DNA sequences lying between short repeated recognition sequences are inverted or exchanged. Again, while offering significant benefits, these methods have significant drawbacks. Homology mediated events generally require large (multi kilobase) regions of sequence similarity, while Cre or FLP recombinase mediated events are generally applicable only to sequences lying between the appropriate recognition repeats.

In prokaryotes, and in yeast, homologous recombination is a high efficiency event, and is the most common means of integrating an exogenous sequence into a bacterial or yeast chromosome. These homologous recombination events play a critical role in the repair of damaged DNA and rely significantly on the *E. coli* RecA protein and its homologues. RecA protein is a DNA binding protein that binds single stranded DNA with high efficiency regardless of nucleotide sequence. After binding of a single stranded DNA molecule and alignment with regions of similarity in a target sequence, RecA mediates strand exchange between two DNA substrates resulting in a homologous recombination event. The regions of similarity required in the RecA mediated event are 1–2 orders of magnitude smaller than those required by the multicellular eukaryotic processes described above.

The present invention provides solutions to many of the problems noted above, including providing site-specific integration of nucleic acids into plants. These and other advantages will be clarified by complete review of the following disclosure.

SUMMARY OF THE INVENTION

The present invention takes advantage of the recombinatorial properties of RecA and other recombinases to mediate the high efficiency integration of transgenes into predetermined sites within a host genome. Evolved recombinases with enhanced recombinatorial or other properties are used to mediate homologous recombination between exogenous DNA substrates and a desired site of insertion in a host chromosome. By allowing for integration into a desired insertion site without rigorous sequence requirements, the present invention significantly broadens the cases in which homologous recombination applies to the production of transgenic organisms. This facilitates the development of transgenic plants and animals with genetic alterations such as gene "knock-outs", gene replacements, co-segregating transgene arrays, and novel exogenous/endogenous promoter-structural gene combinations in addition to randomly inserted transgenes.

In one aspect, the invention provides methods of evolving recombinase proteins which complement the Agrobacterium virE2 gene. To evolve recombinase proteins that complement virE2, one or more recombinase encoding nucleic acids are first diversified by any of a variety of methods. For example, such methods can entail supplying fragments of recombinase gene homologues derived from a variety of sources, recombining them in silico, in vitro or in vivo, and reconstructing a recombinant recombinase gene (by PCR based recursive elongation or other reconstruction methods), to generate a library of recombinase gene homologues. Recombination can be performed recursively for one or more cycle. The resulting library of recombinant nucleic acids is then screened to identify novel recombinase gene homologues that encode proteins which can substitute functionally for the Agrobacterium virE2 gene. In some embodiments, homologues of bacterial recA genes are given. In others, eukaryotic recombinases, such as Rad51 and Dmc1 are provided. Other embodiments provide for the use of evolved Agrobacterium Virulence proteins which have recombinase activity. A preferred embodiment provides for VirE2 proteins which have recombinase activity. In one embodiment, screening of the recombinase library is performed by expressing the recombinase protein homologues in a VirE2 deficient agrobacterium. In another embodiment, screening is performed by expressing the library in plant cells which are infected by VirE2 deficient agrobacterium.

The invention further provides methods of evolving RecA/VirE2 fusion proteins. These methods involve diversifying, e.g., recombining, recA and virE2 gene homologues in silico, in vitro or in vivo to establish a library of hybrid DNA molecules which encode RecA/VirE2 fusion proteins. This library is screened to identify RecA/VirE2 fusion proteins which maintain both RecA and VirE2 functional activities.

The present also invention provides for libraries of recombinant recombinase gene homologues and hybrid recA/virE2 genes.

In another aspect, the invention provides for recombinase proteins which have evolved VirE2 activity. In a preferred embodiment the evolved recombinase protein has a nuclear localization signal, and in one preferred embodiment, this nuclear localization signal is derived from VirE2.

Other embodiments provide for RecA/VirE2 fusion proteins that exhibit both RecA and VirE2 functional activities. In preferred embodiments, the RecA/VirE2 fusion protein has a nuclear localization signal, optionally derived from VirE2.

Other aspects of the invention provide for transgenic organisms expressing evolved recombinase and RecA/VirE2 fusion proteins. In preferred embodiments, these organisms are transgenic plants. These transgenic plants are chosen from among species of experimental, agronomic, and horticultural interest.

The invention further provides for Agrobacterium strains expressing recombinase genes. In some embodiments, the recombinase gene is located on a plasmid. In preferred embodiments this plasmid is a helper plasmid of a binary vector system. In other embodiments the recombinase gene is integrated into an agrobacterium chromosome. Preferred embodiments provide for Agrobacterium strains expressing recombinase proteins that are homologues of one or more of RecA, Rad51 or Dmc1.

Other embodiments provide for Agrobacterium strains expressing RecA/VirE2 fusion proteins. In some cases DNAs encoding the fusion protein, are located on one or more plasmid, and in preferred embodiments, this plasmid is a helper plasmid of a binary vector system. Alternatively, DNA encoding a fusion protein is integrated into an agrobacterium chromosome.

In another aspect, the invention provides methods of integrating transgenes into a pre-determined locus of a prokaryotic or eukaryotic chromosome. Such methods entail introducing an exogenous DNA sequence which shares a region of sequence similarity with a desired insertion site along with an evolved recombinase protein into a cell of choice. In a preferred embodiment, the exogenous DNA is cloned adjacent to a right T-DNA border, and preferably between T-DNA borders, into an agrobacterium strain that expresses either a recombinase protein or a RecA/VirE2 fusion protein. The T-DNA comprising the exogenous DNA and the recombinase, or, alternatively, the RecA/VirE2 fusion protein are targeted to the plant cell nucleus where the exogenous DNA is integrated into the chromosome at a predetermined locus. In some embodiments, the transgenic cell is then regenerated to produce a multicellular transgenic organism.

In a preferred embodiment, the recombinase protein is a VirE2 complementary recombinase protein homologue. In an especially preferred embodiment, the VirE2 complementary recombinase is a RecA, a Rad51 or a Dmc1 protein homologue. In another preferred embodiment, the Agrobacterium strain expresses a RecA/VirE2 fusion protein which maintains both RecA and VirE2 functional activities. In especially preferred embodiments, the RecA or RecA/VirE2 fusion proteins have nuclear localization signals.

These methods are used to integrate transgenes of various types, including but not exclusively: non-functional alleles of endogenous genes to produce "knock-outs;" improved or modified alleles of endogenous genes to produce gene replacements; tissue specific promoters or enhancers targeted to endogenous structural loci to confer tissue or temporal specificity; and integration of exogenous DNA sequences targeted to transgene insertion sites to produce co-segregating arrays of transgenes.

The invention further provides transgenic organisms, including animals, fungi, and plants, e.g., produced by the above-described methods. Transgenic plants of experimentally, agronomically, and horticulturally important species are provided. Examples include transgenic plants which are crop plants.

Another aspect of the invention relates to the identification of novel gene products which influence the integration of transgenes into plant chromosomes by homologous recombination. Using the screening and/or selection methods of the invention, libraries derived from bacterial and eukaryotic sources are assayed for the ability to stimulate integration of T-DNA sequences by homologous recombination.

DETAILED DISCUSSION OF THE INVENTION

The present invention provides methods for evolving novel recombinases that complement the Agrobacterium virE2 gene using a variety of diversification strategies, such as recursive recombination or "nucleic acid shuffling." In preferred embodiments, such recombinases are homologues of the bacterial recA and eukaryotic Rad51 and Dmc1 genes. In other preferred embodiments, the recombinases are RecA/VirE2 fusion proteins or VirE2 proteins that demonstrate recombinase activity. Evolved VirE2 complementary recombinases are used to produce transgenic cells and organisms. In some embodiments, these recombinases are used in the context of Agrobacterium mediated transformation to produce transgenic plants which have integrated a transgene into a predetermined site in their genome. Such targeted transgene insertions occur by homologous recombination facilitated by the evolved recombinases. Recombinases, such as RecA, bind to an exogenous DNA molecule, are involved in a search for similarity, and mediate strand exchange and recombination. Another aspect of the invention relates to plants which express a recombinase transgene which complements VirE2, while other aspects of the present invention relate to organisms, in addition to plants, which are produced by means of evolved recombinase proteins.

Definitions

Unless defined otherwise, all scientific and technical terms are understood to have the same meaning as commonly used in the art to which they pertain. For the purpose of the present invention the following terms are defined below.

The term "shuffling" is used herein to indicate recombination between non-identical sequences. For example, "DNA shuffling" involves recombination of deoxyribonucleic acid (DNA) segments. In some embodiments shuffling may include crossover via homologous recombination or via non-homologous recombination, such as via cre/lox and/or flp/frt systems. Shuffling can be carried out by employing a variety of different formats, including for example, in vitro and in vivo shuffling formats, in silico shuffling formats, shuffling formats that utilize either double-stranded or single-stranded templates, primer based shuffling formats, nucleic acid fragmentation-based shuffling formats, and oligonucleotide-mediated shuffling formats, all of which are based on recombination events between non-identical sequences and are described in more detail or referenced herein below, as well as other similar recombination-based formats. In one class of embodiments, nucleic acid shuffling involves the recursive recombination of nucleic acid sequences.

"Screening" is, in general, a two-step process in which one first determines which cells, organisms or molecules, do and do not express a screening marker, or phenotype (or a selected level of marker or phenotype), and then physically separates the cells, organisms or molecules, having the desired property. Selection is a form of screening in which identification and physical separation are achieved simultaneously by expression of a selection marker, which in some genetic circumstances, allows cells expressing the marker to survive while other cells die (or vice versa). Screening markers include luciferase, β-glucuronidase, green fluorescent protein and neoplastic growth. Selection markers include drug and toxin resistance genes.

The term "gene" is used broadly to refer to any segment of a genomic nucleic acid associated with a biological function. Thus, genes include coding sequences and/or the regulatory sequences required for their expression. Genes also include nonexpressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "Tissue specific" promoter or enhancer is one which regulates transcription in a specific tissue type or cell type, or types.

A "wild-type" gene, or DNA or RNA sequence, is a gene, or sequence that occurs in an organism in nature.

A "transgene" is a gene foreign (or heterologous) to the cell, or homologous to the cell, but in a position within a host cell nucleic acid in which the element is not ordinarily found. A "transgenic" organism is one which has a transgene introduced into its genome. Such an organism may be either an animal or a plant. The site at which a transgene is located in the genome is referred to as its "site of insertion" or alternatively, its "insertion site".

"Transformation" refers to the process by which a transgene is introduced into a cell or organism. An organism is said to be "transformed" if it is the recipient of nucleic acid from an exogenous source, including a virus or bacterium.

"Agrobacterium" are soil-borne plant-pathogenic bacterium, the two predominant species of which are *A. tumefaciens* and *A. rhizogenes*. Agrobacterium carry a tumor causing plasmid designated Ti, modified versions of which serve as common plant vectors. During infection, the "T region," a portion of the Ti plasmid from which "T-DNA" is derived is transferred, along with any intervening sequences, to the host plant cell. Imperfect 25 base pair repeat sequences designated the "right T-DNA border" and the "left T-DNA border" define the "T-DNA ends," and are utilized in the transfer of the T-DNA from the agrobacterium to the plant cell.

Also located on the Ti plasmid are the "virulence" or "vir" genes of agrobacterium. The vir genes are regulated by a signal transformtion system in which the product of the virA gene, the VirA protein, acts as sensor to detect secreted molecules from the plant. Binding of a secreted signal molecule and activation of VirA results in modification and activation of the VirG protein which binds to the promoters of other vir genes, so-called "vir promoters" resulting in transcriptional activation of other vir genes.

The VirE2 protein, the product of the virE2 gene of agrobacterium, is a single stranded DNA binding protein which, along with the VirD protein, binds the T-DNA strand and facilitates its transfer to a plant cell nucleus. Both the VirD and VirE proteins have "nuclear localization signals," amino acid sequences which serve to target the protein to the nucleus of a cell.

The term "Agroinfection" refers to the introduction of plant infectious agents, for example, viruses, into plants by Agrobacterium. More generally "agrobacterium mediated transformation" refers to the transfer of any DNA sequences present between T-DNA ends into a plant cell by an agrobacterium.

"Binary vector systems" refers to a two vector system in which Vir function is supplied on a "helper plasmid" to mediate transfer of a T-DNA located e.g., on a modified Ti plasmid.

RecA protein, the product of the bacterial recA gene is a single stranded DNA binding protein which mediates homologous recombination in *E. coli*. Rad51 and Dmc1 are RecA protein homologues isolated from the eukaryote, *Saccharomyces cerevisiae*.

A "fusion protein" refers to a hybrid protein molecule in which regions of one protein are adjacent to regions of a second protein on a single polypeptide molecule.

Introduction

This invention provides a strategy for targeting transgenes to pre-determined loci in the chromosome of plants and other organisms by homologous recombination. Homologues of recombinase proteins are developed which complement the virE2 gene of agrobacterium. When utilized to produce transgenic organisms, these new recombinase proteins mediate high frequency homologous recombination of exogenous DNA sequences with pre-determined sites in the host genome. Prior to the present invention, few methods existed for targeted modification of a plant genome. The ability to efficiently target pre-determined sites in a plant genome considerably expands the repertory of commercially relevant modifications of plant species. In the current invention, Agrobacterium mediated transformation is used to deliver single stranded DNA and recombinase protein to mediate homologous recombination of T-DNA with a plant chromosome. Additionally, recombinases with improved characteristics are used to target exogenous DNA sequences to a predetermined site in the chromosomes of other organisms, including prokaryotes and eukaryotes.

General texts which describe molecular biological techniques useful herein, including the use of vectors, promoters and many other relevant topics related to, e.g., the cloning and expression of recombinases, fusion proteins, and evolved proteins, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (2nd Ed.), Vol. 1–3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2000)("Ausubel")). Similarly, examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as Mullis et al., (1987) U.S. Pat. No. 4,683,202; PCR Protocols A Guide to Methods and Applications (Innis et al. eds) Academic Press Inc. San Diego, Calif. (1990) (Innis); Amheim & Levinson (Oct. 1, 1990) C&EN 36–47; The Journal Of NIH Research (1991) 3, 81–94; (Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem 35, 1826; Landegren et al., (1988) Science 241, 1077–1080; Van Brunt (1990) Biotechnology 8, 291–294; Wu and Wallace, (1989) Gene 4, 560; Barringer et al. (1990) Gene 89, 117, and Sooknanan and Malek (1995) Biotechnology 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

The present invention also relates to host cells and organisms that are transformed with vectors of the invention, and the production of polypeptides of the invention, e.g., evolved recombinases, by recombinant techniques. Host cells are genetically engineered (i.e., transformed, transduced or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for such activities as, for example, activating promoters or selecting transformants. The culture conditions, such as temperature, pH and the like, are those previously used with the host cell selected for expression, and will be apparent to those skilled in the art and in the references cited herein, including, e.g., Freshney (1994) Culture of Animal Cells, a Manual of Basic Technique, third edition, Wiley-Liss, New York and the references cited therein.

The present invention also relates to the production of transgenic organisms, which may be bacteria, yeast, fungi, animals or plants. While a thorough discussion of techniques relevant to bacteria, unicellular eukaryotes and cell culture may be found in references enumerated above, additional techniques valuable in the production of transgenic animals also include, e.g., Hogan et.al., Manipulating the Mouse Embryo, second edition, (1994) Cold Spring Harbor Press, Plainview.

Transforming Nucleic Acids Into Plants.

Preferred embodiments of the invention pertain to the targeted insertion of exogenous DNA sequences mediated by novel and existing recombinases. Techniques for transforming plant cells with nucleic acids are generally available and can be adapted to the invention by the introduction of nucleic acids encoding recombinases, fusion proteins and evolved proteins. In addition to Berger, Ausubel and Sambrook, useful general references for plant cell cloning, culture and regeneration include Jones (ed) (1995) Plant Gene Transfer and Expression Protocols—Methods in Molecular Biology, Volume 49 Humana Press Towata, N.J. ("Jones"); Payne et al. (1992) Plant Cell and Tissue Culture in Liquid Systems John Wiley & Sons, Inc. New York, N.Y. ("Payne"); and Gamborg and Phillips (eds) (1995) Plant Cell, Tissue and Organ Culture; Fundamental Methods Springer Lab Manual, Springer-Verlag (Berlin Heidelberg New York) ("Gamborg"). A variety of cell culture media are described in Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in R. R. D. Croy, Ed. (1993)Plant Molecular Biolgy Bios Scientific Publishers, Oxford, U.K.

The nucleic acid constructs of the invention, e.g., recombinases, fusion proteins, and evolved proteins, are introduced into plant-cells, either in culture or in the organs of a plant by a variety of conventional techniques. To use evolved sequences, recombinant DNA vectors suitable for transformation of plant cells are prepared. A DNA sequence coding for a desired evolved, e.g., shuffled, recombinase DNA is transformed into the plant. Where the sequence is expressed, the sequence is optionally combined with transcriptional and translational initiation regulatory sequences which further direct the transcription or translation of the sequence from the recombinant, e.g., shuffled, gene in the intended tissues of the transformed plant. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting e.g., cells, embryos, and protoplasts, are known in the art and well described in the scientific and patent literature. For example, a number of methods are described in Jones (ed) (1995) Plant Gene Transfer and Expression Protocols—Methods in Molecular Biology, Volume 49 Humana Press Towata N.J., as well as in the other references noted herein and available in the literature.

For example, the introduction of DNA constructs using polyethylene glycol precipitation is described in Paszkowski, et al., EMBO J. 3:2717 (1984). Electroporation techniques are described in Fromm, et al., Proc. Nat'l. Acad. Sci. USA 82:5824 (1985). Ballistic transformation techniques are described in Klein, et al., Nature 327:70–73 (1987). Additional details are found in Jones (1995) supra.

Agrobacterium Mediated Transformation

In preferred embodiments, DNA constructs are combined with suitable T-DNA flanking regions and introduced into a conventional Agrobacterium host vector. The virulence functions of the Agrobacterium host directs the insertion of the construct, for example, any one or more of the following are optionally combined with T-DNA flanking sequences: a coding sequence; a non-coding sequence; a structural gene; a disabled gene; a promoter; and an enhancer and adjacent marker into the plant cell DNA when the cell is infected by the bacteria. Agrobacterium-mediated transformation techniques, including disarming and use of binary vectors, are also well described in the scientific literature. See, for example Horsch, et al., "A simple and general method for transferring genes into plants." Science 233:496–498 (1984), and Fraley, et al., "Expression of bacterial genes in plant cells." Proc. Nat'l. Acad. Sci. USA 80:4803 (1984) and recently reviewed in Hansen and Chilton, "Lessons in gene transfer to plants by a gifted microbe." Current Topics in Microbiology 240:22–51 (1998) and Das, "DNA transfer from Agrobacterium to plant cells in crown gall tumor disease." Subcelular Biochemistry 29: Plant Microbe Interactions:343–363 (1998). These techniques are adapted to the present invention by the introduction of recombinases, such as RecA to replace or augment VirE2 function, and the use of such modified agrobacterium strains in the production of transgenic plants and fungi.

Agrobacteria are gram-negative, soil-borne plant pathogens that cause neoplastic growth in susceptible plants. The most prevalent pathogenic strains, *Agrobacterium tumefaciens* and *Agrobacterium rhizogenes* cause crown gall and hairy root disease, respectively. In recent years, the art of plant transgenesis has taken advantage of genetically modified agrobacterium strains to transfer exogenous DNA to host plants by means of agrobacterium mediated transformation. The process of agrobacterium mediated transformation takes advantage of the naturally occurring DNA transfer system of these pathogenic bacteria.

Genes located on the Ti, or "tumor inducing", plasmid of *A. tumefaciens*, are required for DNA transfer and tumor induction. The transferred DNA or T-DNA is derived from the T-region of the Ti plasmid. This region is delimited by the presence of two imperfect 25 base pair repeats designated T-DNA borders. DNA sequences, including the exogenous sequences selected for targeting to a plant genome of the invention, can be cloned between the T-DNA borders and subsequently transferred to a host plant cell. Alternatively, the exogenous sequence can be cloned adjacent to a single right T-DNA border and transferred to the host plant cell.

The virulence, or vir, gene products activate and facilitate transfer of T-DNA to a host plant cell. VirA is a transmembrane protein which acts as a sensor, detecting the presence of molecules, such as acetosyringone (3',5'-dimethosy-4'-hydroxyacetophenone), which are secreted by wounded or metabolically active target cells. When activated by such molecules, VirA exhibits kinase activity that activates the VirG protein. In turn, VirG induces transcription of the virB, virC, VirD and virE operons. The VirB proteins are thought to form a conjugation-like pore in the bacterial surface through which the T-DNA passes upon transfer. VirC, VirD and VirE proteins are involved in the production and transfer of the T-DNA strand. In the present invention, VirE functions are augmented or alternatively, replaced by evolved recombinases or fusion proteins which possess both recombinase and VirE2 activities.

As the T-DNA is released from the plasmid, the VirD2 protein binds the right T-DNA border. Essential for effective transformation, VirE2 function is transported to the host plant cell by the Agrobacterium. While it is clear that VirE2 is involved in integration of the T-DNA into the host cell chromosome, it does not appear to be essential for transfer of the T-DNA from the Agrobacterium to the host cell, and may be supplied by a second Agrobacterium or by the host cell itself, (Ream "Import of *Agrobacterium tumefaciens* virulence proteins and transferred DNA into plant cell nuclei." Subcellular Biochemistry 29: Plant-Microbe Interactions:365–384 (1998), and references therein). Multiple molecules of VirE2, a single stranded DNA binding protein, then bind to the T-DNA strand. Both VirD2 and VirE2 possess nuclear localization signals thought to facilitate targeting of the T-DNA to the host plant cell nucleus, where the T-DNA is integrated into the plant cell nucleus. The present invention provides for the replacement and/or augmentation of VirE2 by VirE2 complementary recombinases, such as RecA proteins and RecA/VirE2 fusion proteins. These novel recombinases fulfill the role of VirE2 in transformation and mediate integration of the transferred T-DNA strand into a predetermined locus by homologous recombination.

Binary Vector Systems

Because the vir gene products are soluble factors, their function is optionally supplied in trans, giving rise to the use of binary vector systems in the production of transgenic plants. In a binary vector system, vir genes are supplied on a helper plasmid, often a disarmed Ti plasmid, or alternatively, integrated into an Agrobacterial chromosome. A disarmed Ti plasmid which lacks the genes that mediate oncogenesis is much reduced in size from the native 200 kilobase pairs. The exogenous DNA sequence, for example, a plant or bacterial structural gene, or a plant or viral promoter or enhancer, is cloned between T-DNA border repeats on a second plasmid, which typically also has a marker, e.g. an antibiotic resistance gene, to facilitate selection after introduction into Agrobacterium. Subsequently, the exogenous DNA sequence is transferred as part of the T-DNA strand to a host plant (or plant cell or explant) where it integrates into a random site in the host plant chromosome. In an embodiment of the invention, a binary vector system employing a VirE2 complementary recombinase protein cloned into a helper plasmid is used to mediate transfer of T-DNA. In an alternative embodiment, a RecA/VirE2 fusion protein is used to mediate transfer of T-DNA. In both of these embodiments, use of the novel recombinase or RecA/VirE2 fusion protein facilitates integration of the T-DNA by homologous recombination.

The use of agrobacterium mediated transfer has proven a valuable technique in the production of genetically modified plant species. In addition to their utility in the transformation of plant species, Agrobacterium are readily manipulated in vitro by well established techniques of molecular biology. Such techniques are well known to those skilled in the art, and are referenced in e.g., Ausubel, Sambrook, and Berger, supra; Croy (ed) (1993) Plant Molecular Biology, Bios Scientific Publishers, Oxford, U.K., and Jones (ed) (1995) Plant Gene Transfer and Expression Protocols—Methods in Molecular Biology, Volume 49 Humana Press, Towata, N.J. These are useful in the context of the present invention for the manipulation and culture of Agrobacterium cells, transformation techniques, and techniques useful for the analysis of plant cells subject to agrobacterium mediated transformation.

While dicotyledonous plants have proven most amenable to manipulation by agrobacterium mediated transformation, reports of transformation of important monocotyledonous crop plants have been forthcoming. In addition, Agrobacterium strains which are capable of transforming fungal species have also been described. Agrobacterium Vir proteins have been used to target DNA to the nucleus of mammalian cells as well. The present invention makes use of this valuable technique to produce transgenic plants, animals and fungi which have integrated an exogenous DNA sequence into a predetermined site in their genome, i.e., using the VirE2 complementary recombinases and fusion proteins of the invention to provide site-specific integration.

Regeneration of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., Protoplasts Isolation and Culture, Handbook of Plant Cell Culture, pp. 124–176, Macmillian Publishing Company, New York, (1983); and Binding, Regeneration of Plants, Plant Protoplasts, pp. 21–73, CRC Press, Boca Raton, (1985). Regeneration can also be obtained from plant callus, explants, somatic embryos (Dandekar, et al., J. Tissue Cult. Meth. 12:145 (1989); McGranahan, et al., Plant Cell Rep. 8:512 (1990)), organs, or parts thereof. Such regeneration techniques are described generally in Klee, et al., Ann. Rev. of Plant Phys. 38:467–486 (1987). Additional details are found in Payne (1992) and Jones (1995), both supra. These methods are adapted to the invention to produce transgenic plants which have incorporated novel recombinase genes, as well as in the production of transgenic plants having transgenes inserted at a predetermined site using the novel recombinases of the invention.

Preferred plants for the transformation and expression of the novel recombinases of this invention include agronomically and horticulturally important species. Such species include, but are not restricted to members of the families: Graminae (including corn, rye, triticale, barley, millet, rice, wheat, oats, etc.); Leguminosae (including pea, beans, lentil, peanut, yam bean, cowpeas, velvet beans, soybean, clover, alfalfa, lupine, vetch, lotus, sweet clover, wisteria, and sweetpea); Compositae (the largest family of vascular plants, including at least 1,000 genera, including important commercial crops such as lettuce, safflower, and sunflower) and Rosaciae (including raspberry, apricot, almond, peach, rose, etc.), as well as nut plants (including, walnut, pecan, hazelnut etc.)

Additionally, preferred targets for modification by transgenes inserted to a predetermined site in the genome include, as well as those specified above, plants from the genera: Agrostis, Allium, Antirrhinum, Apium, Arachis, Asparagus, Atropa, Avena (e.g., oats), Bainbusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum (e.g., barley), Hyoseyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Ortyza (e.g., rice), Panicum, Pelargonium, Pennisetum (e.g., millet), Petunia, Pisum, Phaseolus, Phleum, Poa, Prunus, Ranunculus, Raphanus, Ribes, Ricinus, Rubus, Saccharum, Salpiglossis, Secale (e.g., rye), Senecio, Setaria, Sinapis, Solanum, Sorghum, Stenotaphrum, Theobroma, Trifolium, Trigonella, Triticum (e.g., wheat), Vicia, Vigna, Vitis, Zea (e.g., corn), and the Olyreae, the Pharoideae and many others. As noted, plants in the family Gramineae are a particularly preferred target plants for the methods of the invention.

Common crop plants which are targets of the present invention include corn, rice, triticale, rye, cotton, soybean, sorghum, wheat, oats, barley, millet, sunflower, canola, peas, beans, lentils, peanuts, yam beans, cowpeas, velvet beans, clover, alfalfa, lupine, vetch, lotus, sweet clover, wisteria, sweetpea and nut plants (e.g., walnut, pecan, etc).

In construction of recombinant expression cassettes of the invention, which include, for example, helper plasmids comprising VirE2 function, and plasmids comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters which direct transcription in plant cells are suitable. The promoter can be either constitutive or inducible. In addition to the promoters noted above, promoters of bacterial origin which operate in plants include the octopine synthase promoter, the nopaline synthase promoter and other promoters derived from native Ti plasmids. See, Herrara-Estrella et al. (1983), Nature, 303:209–213. Viral promoters include the 35S and 19S RNA promoters of cauliflower mosaic virus. See, Odell et al. (1985) Nature, 313:810–812. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer, (1988) EMBO J. 7:3315–3327. Many other promoters are in current use and can be coupled to an exogenous DNA sequence to direct expression of the nucleic acid.

If expression of a polypeptide, including the recombinase or fusion protein of the present invention, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically comprise a nucleic acid subsequence which confers a selectable phenotype on plant cells. The vector comprising the sequence will typically comprise a marker gene which confers a selectable phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos and Basta). For example, crop selectivity to specific herbicides can be conferred by engineering genes into crops which encode appropriate herbicide metabolizing enzymes from other organisms, such as microbes. See, Padgette et al. (1996) "New weed control opportunities: Development of soybeans with a Round UP Ready™ gene" In: Herbicide-Resistant Crops (Duke, ed.), pp 53–84, CRC Lewis Publishers, Boca Raton ("Padgette, 1996"); and Vasil (1996) "Phosphinothricin-resistant crops" In: Herbicide-Resistant Crops (Duke, ed.), pp 85–91, CRC Lewis Publishers, Boca Raton) (Vasil, 1996).

The invention described herein furthers the current technology by providing for high efficiency integration at a predetermined site in the host genome. One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Site Specific Intergration of Transgenes

An aspect of the present invention pertains to the production of transgenic organisms, other than plants which have integrated an exogenous DNA sequence into a predetermined site in their genome. The present invention makes use of evolved recombinase molecules to mediate the integration of exogenous sequences sharing only limited regions of sequence similarity with the selected target site. In the invention, exogenous DNA sequences are introduced in concert with evolved recombinase proteins, into cells of either prokaryotic or eukaryotic origin. The evolved recombinase proteins bind the exogenous DNA sequence and mediate strand exchange with sequences sharing a limited region of similarity in the host genome. Use of such recombinases reduces the length of sequence similarity required while still permitting introduction of a transgene or other modification at a wild-type locus.

Techniques well known in the production of transgenic cells and animals, (see e.g., Hogan et.al., Manipulating the Mouse Embryo, second edition, (1994) Cold Spring Harbor Press, Plainview), utilize homologous recombination to introduce site specific modifications of an animal genome. Most commonly, the animal is a mouse. Typically such techniques rely on multiple large regions (>5–10 kb) of sequence similarity, coupled with stringent selection protocols, to increase the frequency of targeted transgene insertions. The present invention reduces the requirement for extensive regions of sequence similarity by using evolved recombinases, such as evolved RecA proteins or Rad51 proteins to mediate a homology search and subsequent recombination.

Widespread use of targeted genetic modification in plants has lagged behind the manipulation of mammalian genomes described above. Offringa et al. (U.S. Pat. No. 5,501,967) postulate the use of agrobacterium T-DNA constructs with regions of sequence similarity between T-DNA borders. They report homologous recombination between an exogenous DNA sequence with a selectable marker and a previously integrated transgene sharing regions of sequence similarity. A single homologous recombinant was obtained, demonstrating that while theoretically possible, site specific integration by homologous recombination was a low frequency event. In the example given, the integrated target transgene was present as a inverted duplication, a configuration that may enhance the frequency of recombination at the site. The present invention removes the restriction that the site chosen for integration of the exogenous DNA sequence is a transgene insertion site. By employing the evolved recombinases or fusion proteins of the invention, recombination between an exogenous sequence and a wild-type locus is facilitated.

Odell et al. (U.S. Pat. No. 5,658,772) and Hooykaas et al. (U.S. Pat. No. 5,635,381) involve the use of the Cre recombinase system in agrobacterium, and provide for various constructs and strains which express the Cre recombinase and which are capable of mediating recombination of sequences lying between loxP sites. While these methods readily enable manipulation of a genetic locus defined by a transgene having loxP sites, they are less suited to targeting of transgenes to wild-type chromosomal loci. The recombinases and fusion proteins of the present invention and the methods using them to produce transgenic plants readily target exogenous sequences to wild-type loci sharing only a limited region of sequence similarity with the exogenous sequence.

The ability to readily target exogenous DNA sequences to pre-defined loci in a plant genome has numerous commercial applications in agronomically and horticulturally relevant plant species. In some of these cases, targeting of an exogenous sequence to a previously established transgene insertion site is of great value. For example, the production of genetically modified crop plants frequently requires the co-integration and selection of an antibiotic resistance gene or other marker. Such markers have raised widespread ecological concern which could be alleviated by the removal of the resistance gene or marker, or its replacement with a non-functional or inert DNA sequence.

Likewise, by introducing a subsequent transgene or transgenes to the same locus as a previously integrated transgene by site-specific recombination guided by the choice of the transgene as the target site, greatly simplified plant breeding and hybridization programs could be achieved. By having to breed only a single locus onto a chosen genetic background rather than independently breeding multiple integration sites, the number of generations required to obtain a strain of plant with a desirable complex phenotype would be drastically reduced.

However, other applications require the introduction of exogenous DNA sequences to a pre-determined but wild-type genetic locus. For example, in order to effectively alter a phenotype, a wild-type chromosomal gene may need to be completely inactivated. Current use of antisense or cosuppressor technology can significantly reduce the expression of a specified gene, but does not always eliminate its expression entirely. Inactivation of the endogenous gene by disrupting it or replacing it with an otherwise non-functional copy could achieve this elimination of expression. The present invention provides for VirE2 complementary recombinase proteins and RecA/VirE2 fusion proteins which mediate targeted insertion of T-DNAs into pre-determined locations in the host chromosome, relying on short regions (approximately 50–1000 nucleotides) of sequence similarity. It is not presumed, nor is it required that the desired insertion site be the site of a prior insertion or other alteration. This significantly extends the potential applications available through the use of this technology.

The invention makes it possible to replace an endogenous gene with one that has been modified or improved. For example, to alter the substrate specificity of an endogenous plant enzyme, one could replace the endogenous gene with an altered gene exhibiting different substrate specificities. In the absence of gene replacement technology, one can only add to the activity of endogenous enzymes by adding new substrate specificities. However, the endogenous enzyme could still act on its original substrate reducing efficiency or yield of the modified enzyme. Alternatively, one could replace the promoter or other regulatory regions of genes to change the tissue specificity of expression, or increase, or decrease expression of the genes. This allows researchers to determine the effects of specific mutations in genes and promoters in a manner not possible using existing transgenic technologies as well as permitting the development of commercial phenotypes not possible by simply adding a new gene without replacement of the endogenous gene.

Additionally, in situations where it is not desirable to replace an endogenous gene, it can, nonetheless, be desirable to target transgenes to specific chromosomal locations. The expression levels experienced from Agrobacterium transformation of plants varies widely between transformation events. The ability to target transgenes to specific chromosomal locations provided for by the present invention, will allow researchers to identify those locations that are favorable for the desired expression level, and insert the transgene in that specific chromosomal location.

Homologous Recombination

In bacteria and yeast, integration of exogenous DNA sequences occurs most prevalently by homologous rather than heterologous recombination. In these cases, production of transgenic organisms is readily accomplished and typically results in an insertion event that is targeted to a corresponding endogenous locus. The present invention extends this efficient and homologous recombination process to other fungi and multicellular eukaryotes, in addition to allowing for improvements in efficiency of transfer or integration by novel recombinase proteins.

Homologous recombination is a multistep process which requires a search for and recognition of sequence similarity, and exchange between the two DNA molecules undergoing recombination. In *E.coli*, the process of homologous recombination is largely mediated by the RecA protein. For a recent review, see, e.g., Roca and Cox., Prog. Nucl. Acid. Res. 56:129–223 (1997), and references therein. Similarly, the RecA homologues Rad51 and Dmc1 have been shown to fulfill comparable functions in the yeast *Saccharomyces cerevisiae*, see, e.g., Shinahara et.al., Cell 69:457–470 (1992); and Bishop et.al., Cell 69:439–456 (1992).

RecA is a sequence independent single stranded DNA binding protein that coats single stranded DNA to form a nucleoprotein filament. In this nucleoprotein filament, one monomer of RecA protein is bound to about 3 nucleotides. Initial pairing of DNA molecules sharing sequence similarity can occur anywhere along the length of the DNA substrate and is generally a rapid process. This pairing involves the association of one single-stranded and one double stranded DNA molecule to form a transient triplex DNA intermediate. RecA has three distinct DNA binding sites and can bind up to three DNA strands within a filament groove. The first site is thought to bind single stranded DNA with high affinity, a duplex strand complementary to the first strand is bound by the second site, while the third site accommodates the strand displaced during the exchange process. RecA appears to stabilize recombination intermediates, promoting strand exchange. In the invention, the ability of RecA and other recombinases to mediate homologous recombination is utilized to advantage to develop novel recombinase proteins with improved properties. Evolved recombinases and fusion proteins that complement agrobacterium VirE2 protein extend the utility of such recombinases as RecA to the production of transgenic organisms including multicellular eukaryotes.

In addition to the yeast homologues specified above, RecA homologues have been isolated from a broad range of eukaryotic species, including, fungus, plants and animals. For examples see: Bezzubova et.al., Nucl. Acids. Res. 21:1577–1580 (1993), Cerutti et.al., Proc. Natl. Acad. Sci. USA 89:8068–8072 (1992), Morita et.al., Proc. Natl. Acad. Sci. USA 90:6577–6580 (1993). *E.coli* RecA has been expressed in plant cells and was shown to enhance recombination/repair activity in response to mitomycin C damage and to increase intrachromosomal recombination when targeted to the nucleus (Reiss et. al., Proc. Natl. Acad. Sci. USA 93:3094–3098 (1996)). These results demonstrate that bacterial RecA protein is functional in the context of a multicellular eukaryote, and is capable of interacting with the endogenous cellular machinery to carry out homologous recombination. The present invention utilizes recombinases, such as bacterial RecA and its many homologues as a natural source of diversity for the evolution of improved RecA proteins and RecA fusion proteins.

Diversity Generation

The invention provides for the evolution of novel recombinase proteins, such as RecA homologues, which have acquired the property of providing VirE2 protein function in deficient agrobacterium and plant cells. Techniques for evolving DNA molecules to acquire a desired property using a variety of diversity generating procedures, e.g., DNA shuffling, are available and described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids that encode proteins with or which confer desirable properties. Following diversification by one or more of the methods herein, or otherwise available to one of skill, any nucleic acids that are produced can be selected for a desired activity or property, e.g. testing for and identifying any of the usual VirE2 or recombinase activities, by any of the assays in the art. This can include identifying any activity that can be detected, for example, in an automated or automatable format, by any of the assays in the art, e.g., by assaying complementation in virE2 deficient agrobacterium. A variety of related (or even unrelated) properties can be evaluated, in serial or in parallel, at the discretion of the practitioner.

Descriptions of a variety of diversity generating procedures which can be used for generating modified nucleic acid sequences encoding recombinases that complement VirE2 function are found the references cited therein: Stemmer, et al. (1999) "Molecular breeding of viruses for targeting and other clinical properties" Tumor Targeting 4:1–4; Ness et al. (1999) "DNA Shuffling of subgenomic sequences of subtilisin" Nature Biotechnology 17:893–896; Chang et al. (1999) "Evolution of a cytokine using DNA family shuffling" Nature Biotechnology 17:793–797; Minshull and Stemmer (1999) "Protein evolution by molecular breeding" Current Opinion in Chemical Biology 3:284–290; Christians et al. (1999) "Directed evolution of thymidine kinase for AZT phosphorylation using DNA family shuffling" Nature Biotechnology 17:259–264; Crameri et al. (1998) "DNA shuffling of a family of genes from diverse species accelerates directed evolution" Nature 391:288–291; Crameri et al. (1997) "Molecular evolution of an arsenate detoxification pathway by DNA shuffling," Nature Biotechnology 15:436–438; Zhang et al. (1997) "Directed evolution of an effective fucosidase from a galactosidase by DNA shuffling and screening" Proc. Natl. Acad. Sci. USA 94:4504–4509; Patten et al. (1997) "Applications of DNA Shuffling to Pharmaceuticals and Vaccines" Current Opinion in Biotechnology 8:724–733; Crameri et al. (1996) "Construction and evolution of antibody-phage libraries by DNA shuffling" Nature Medicine 2:100–103; Crameri et al. (1996) "Improved green fluorescent protein by molecular evolution using DNA shuffling" Nature Biotechnology 14:315–319; Gates et al. (1996) "Affinity selective isolation of ligands from peptide libraries through display on a lac repressor 'headpiece dimer'" Journal of Molecular Biology 255:373–386; Stemmer (1996) "Sexual PCR and Assembly PCR" In: The Encyclopedia of Molecular Biology. VCH Publishers, New York. pp. 447–457; Crameri and Stemmer (1995) "Combinatorial multiple cassette mutagenesis creates all the permutations of mutant and wildtype cassettes" BioTechniques 18:194–195; Stemmer et al., (1995) "Single-step assembly of a gene and entire plasmid form large numbers of oligodeoxy-ribonucleotides" Gene, 164:49–53; Stemmer (1995) "The Evolution of Molecular Computation" Science 270:1510; Stemmer (1995) "Searching Sequence Space" Bio/Technology 13:549–553; Stemmer (1994) "Rapid evolution of a protein in vitro by DNA shuffling" Nature 370:389–391; and Stemmer (1994) "DNA shuffling by random fragmentation and reassembly: In vitro recombination for molecular evolution." Proc. Natl. Acad. Sci. USA 91:10747–10751.

Mutational methods of generating diversity include, for example, site-directed mutagenesis (Ling et al. (1997) "Approaches to DNA mutagenesis: an overview" Anal Biochem. 254(2): 157–178; Dale et al. (1996) "Oligonucleotide-directed random mutagenesis using the phosphorothioate method" Methods Mol. Biol. 57:369–374; Smith (1985) "In vitro mutagenesis" Ann. Rev. Genet. 19:423–462; Botstein & Shortle (1985) "Strategies and applications of in vitro mutagenesis" Science 229:1193–1201; Carter (1986) "Site-directed mutagenesis" Biochem. J. 237:1–7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488–492; Kunkel et al. (1987) "Rapid and efficient site-specific mutagenesis without phenotypic selection" Methods in Enzymol. 154, 367–382; and Bass et al. (1988) "Mutant Trp repressors with new DNA-binding specificities" Science 242:240–245); oligonucleotide-directed mutagenesis (Methods in Enzymol. 100: 468–500 (1983); Methods in Enzymol. 154: 329–350 (1987); Zoller & Smith (1982) "Oligonucleotide-directed mutagenesis using M13-derived vectors: an efficient and general procedure for the production of point mutations in any DNA fragment" Nucleic Acids Res. 10:6487–6500; Zoller & Smith (1983) "Oligonucleotide-directed mutagenesis of DNA fragments cloned into M13 vectors" Methods in Enzymol. 100:468–500; and Zoller & Smith (1987) "Oligonucleotide-directed mutagenesis: a simple method using two oligonucleotide primers and a single-stranded DNA template" Methods in Enzymol. 154:329–350); phosphorothioate-modified DNA mutagenesis (Taylor et al. (1985) "The use of phosphorothioate-modified DNA in restriction enzyme reactions to prepare nicked DNA" Nucl. Acids Res. 13: 8749–8764; Taylor et al. (1985) "The rapid generation of oligonucleotide-directed mutations at high frequency using phosphorothioate-modified DNA" Nucl. Acids Res. 13: 8765–8787 (1985); Nakamaye & Eckstein (1986) "Inhibition of restriction endonuclease Nci I cleavage by phosphorothioate groups and its application to oligonucleotide-directed mutagenesis" Nucl. Acids Res. 14: 9679–9698; Sayers et al. (1988) "Y-T Exonucleases in phosphorothioate-based oligonucleotide-directed mutagenesis" Nucl. Acids Res. 16:791–802; and Sayers et al. (1988) "Strand specific cleavage of phosphorothioate-containing DNA by reaction with restriction endonucleases in the presence of ethidium bromide" Nucl. Acids Res. 16: 803–814); mutagenesis using gapped duplex DNA (Kramer et al. (1984) "The gapped duplex DNA approach to oligonucleotide-directed mutation construction" Nucl. Acids Res. 12: 9441–9456; Kramer & Fritz (1987) Methods in Enzymol. "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987–6999).

Additional suitable methods include point mismatch repair (Kramer et al. (1984) "Point Mismatch Repair" Cell 38:879–887), mutagenesis using repair-deficient host strains (Carter et al. (1985) "Improved oligonucleotide site-directed mutagenesis using M13 vectors" Nucl. Acids Res. 13: 4431–4443; and Carter (1987) "Improved oligonucleotide-directed mutagenesis using M13 vectors" Methods in Enzymol. 154: 382–403), deletion mutagenesis (Eghtedarzadeh & Henikoff(1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415–423), mutagenesis by total gene synthesis (Nambiar et al. (1984) "Total synthesis and cloning of a gene coding for the ribonuclease S protein" Science 223: 1299–1301; Sakamar and Khorana (1988) "Total synthesis and expression of a gene for the a-subunit of bovine rod outer segment guanine nucleotide-binding protein (transducin)" Nucl. Acids Res. 14: 6361–6372; Wells et al. (1985) "Cassette mutagenesis: an efficient method for generation of multiple mutations at defined sites" Gene 34:315–323; and Grundström et al. (1985) "Oligonucleotide-directed mutagenesis by microscale 'shotgun' gene synthesis" Nucl. Acids Res. 13: 3305–3316), double-strand break repair (Mandecki (1986); Arnold (1993) "Protein engineering for unusual environments" Current Opinion in Biotechnology 4:450–455. "Oligonucleotide-directed double-strand break repair in plasmids of *Escherichia coli*: a method for site-specific mutagenesis" Proc. Natl. Acad. Sci. USA, 83:7177–7181). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination." Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION", by del Cardayre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

In brief, several different general classes of sequence modification methods, such as mutation, recombination, etc. are applicable to the present invention and set forth, e.g., in the references above. Any of these methods can be adapted to the present invention to evolve the recombinase and VirE2 homologues discussed herein to produce new recombinases with improved properties. Both the methods of making such recombinases and the recombinases produced by these methods are features of the invention.

The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction (PCR). This process and many process variants is described in several of the references above, e.g., in Stemmer (1994) Proc. Natl. Acad. Sci. USA 91:10747–10751. Thus, nucleic acids encoding recombinases, e.g., recA, dmc1, rad51, etc., can be recombined in vitro to produce a library of recombinant recombinases. For example, nucleic acids encoding RecA variants can be digested with a nuclease such as DNAseI to produce random fragments. Alternatively, the fragments can be produced by mechanical or chemical cleavage. The fragments are denatured, and then annealed, producing partially overlapping duplex DNA molecules. These partial duplex molecules are then extended in a primeness PCR. This cycle is repeated generating a library of full length nucleic acids encoding recombinase variants.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Thus, nucleic acids encoding recombinases can be recombined, e.g., as episomal components within cells to produce novel recombinase homologues.

Whole genome recombination methods can also be used in which whole genomes of cells or other organisms are recombined, optionally including spiking of the genomic recombination mixtures with desired library components (e.g., recA or other recombinase homologue nucleic acids). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18,2000, (PCT/US00/01202); "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579).

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579). Extensive details regarding in silico recombination methods are found in these applications. This methodology is generally applicable to the present invention in providing for recombination of recombinase encoding nucleic acids, including recA, dmc1, and rad51 (as well as any number of additional recombinase homologue nucleic acids) in silico and/or the generation of corresponding nucleic acids or proteins.

A recombinant nucleic acid produced, e.g., by recursively recombining one or more polynucleotide of the invention with one or more additional nucleic acid also forms a part of the invention. The one or more additional nucleic acid may include another polynucleotide of the invention; optionally, alternatively, or in addition, the one or more additional nucleic acid can include, e.g., a nucleic acid encoding a naturally-occurring recA or a subsequence thereof, or any homologous recA sequence or subsequence thereof, or RAD51 or DMC1 sequence or subsequence thereof (e.g., a recA or RAD51 as found in Genbank or other available literature), or, e.g., any other homologous or non-homologous nucleic acid (certain recombination formats noted above, notably those performed synthetically or in silico, do not require homology for recombination).

The recombining steps may be performed in vivo, in vitro, or in silico as described in more detail in the references above. Also included in the invention is a cell containing any resulting recombinant nucleic acid, nucleic acid libraries produced by recursive recombination of the nucleic acids set forth herein, and populations of cells, vectors, viruses, plasmids or the like comprising the library or comprising any recombinant nucleic acid resulting from recombination (or recursive recombination) of a nucleic acid as set forth herein with another such nucleic acid, or an additional nucleic acid. Corresponding sequence strings in a database present in a computer system or computer readable medium are a feature of the invention.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "SINGLE-STRANDED NUCLEIC ACID TEMPLATE-MEDIATED RECOMBINATION AND NUCLEIC ACID FRAGMENT ISOLATION" by Affholter, U.S. Ser. No. 09/656,549, filed Sep. 6, 2000.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" Nature Biotech 17:1205. This approach can be used to generate an initial a library of variants which can optionally serve as a substrate for one or more in vitro or in vivo recombination methods. See, also, Ostermeier et al. (1999) "Combinatorial Protein Engineering by Incremental Truncation," Proc. Natl. Acad. Sci. USA, 96: 3562–67; Ostermeier et al. (1999), "Incremental Truncation as a Strategy in the Engineering of Novel Biocatalysts," Biological and Medicinal Chemistry, 7: 2139–44.

Mutational methods which result in the alteration of individual nucleotides or groups of contiguous or non-contiguous nucleotides can be favorably employed to introduce nucleotide diversity into any recombinase or recombinase related nucleic acid or into VirE2 to generate a population of variants. Many mutagenesis methods are found in the above-cited references; additional details regarding mutagenesis methods can be found in following, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) Technique 1:11–15 and Caldwell et al. (1992) PCR Methods Applic. 2:28–33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) Science, 241:53–57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) Proc. Natl. Acad. Sci. USA 89:7811–7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) Biotechnology Research 11:1548–1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see, Short (1999) U.S. Pat. No. 5,958,672 "PROTEIN ACTIVITY SCREENING OF CLONES HAVING DNA FROM UNCULTIVATED MICROORGANISMS"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above descibed procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" Gene 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "PRODUCTION OF ENZYMES HAVING DESIRED ACTIVITIES BY MUTAGENESIS." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above. "Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" Biotechnology 10:297–300; Reidhaar-Olson et al. (1991) "Random mutagenesis of protein sequences using oligonucleotide cassettes" *Methods Enzymol.* 208:564–86; Lim and Sauer (1991) "The role of internal packing interactions in determining the structure and stability of a protein" *J. Mol. Biol.* 219:359–76; Breyer and Sauer (1989) "Mutational analysis of the fine specificity of binding of monoclonal antibody 51F to lambda repressor" *J. Biol. Chem.* 264:13355–60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

Evolution of Recombinase Protiens

RecA genes have been found in all bacterial strains, including Agrobacterium, in which they have been sought. Diversification, e.g., shuffling of isolated RecA genes and gene homologues, or of bacterial and/or eukaryotic genomes takes advantage of this natural source of molecular diversity from which to recombine and select novel characteristics. For example, hyper-recombinogenic RecA genes have been evolved using DNA shuffling protocols, (Patten, et al., EVOLUTION OF WHOLE CELLS AND ORGANISMS BY RECURSIVE SEQUENCE RECOMBINATION, U.S. patent application Ser. No. 09/354,922 submitted Jul. 15, 1999). Hyper-recombinogenic RecA was selected using a modification of a system developed by Shen et al., Genetics 112, 441–457 (1986); Shen et al., Mol. Gen. Genet. 218, 358–360 (1989) to measure the effect of substrate length and homology on recombination frequency. Shen and Huang's system used plasmids and bacteriophages with small (31–430 base pairs) regions of homology at which the two could recombine. In a restrictive host, only phage that had incorporated the plasmid sequence were able to form plaques.

For evolution of recA, endogenous recA and mutS genes were deleted from a host $E.coli$ strain MC1061. In this strain, no recombination was seen between plasmid and phage. $E.coli$ recA was then cloned into two independent recombination vectors. Plasmids containing cloned RecA were able to recombine phage having regions of sequence similarity ranging from 89–100% identical over 431 base pairs to as little as 31 base pairs with a single base mismatch.

The cloned RecA was then recombined, i.e., shuffled, in vitro using the standard DNase-treatment followed by PCR-based reassembly. Shuffled plasmids were transformed into the non-recombining host strain. These cells were grown up overnight, infected with phage and plated onto growth medium in the presence of a 10-fold excess of MC1061 lacking plasmid. The more efficiently a recA allele promotes recombination between plasmid and phage, the more highly the allele is represented in the bacteriophage DNA. Consequently, harvesting all the phage from the plates and recovering the recA genes selects for the most recombinogenic recA alleles. Recombination frequencies were increased an average of between 5 and 50 fold compared to wild-type RecA, depending on the length of sequence similarity. The most recombinogenic clones yielded recombination frequencies as high as 0.019, a 116 fold increase over wild-type for the best substrate.

The most highly recombinogenic clones can be used as substrates in additional rounds of shuffling, or other diversification procedures, if further improvement in recA is desired. Not all of the variations from the wild-type recA sequence necessarily contribute to the hyper-recombinogenic phenotype. Silent variations can be eliminated by backcrossing.

EXAMPLE

Evolving RecA Genes Which Complement Agrobacterial VirE2.

In the present invention, recombinase genes from various bacterial and eukaryotic sources are diversified, e.g., shuffled in vitro, in vivo, or in silico, using established protocols, to evolve recombinase proteins that complement Agrobacterium VirE2 function. A preferred embodiment of the invention involves evolution of recA genes. Because recombination involves several cellular factors, and because the host RecA equivalent generally interacts better with other host factors than less closely related RecA molecules, it is useful to include RecA homologues from one or more potential target host plant species.

Briefly, in one embodiment, recA gene homologues from various bacterial and eukaryotic sources are treated with a DNAse, and allowed to recombine at regions of sequence similarity. Alternatively, or in addition, oligonucleotides corresponding to recA homologues are synthesized. The polymerase chain reaction is then used to replicate partially overlapping duplex DNA giving rise to DNA segments encoding novel recombinant RecA protein homologues. The population of DNA segments generated in this step constitutes a library of recA DNA segments. This library is cloned into an appropriate helper plasmid, e.g. pRK310, which is introduced into a mutant agrobacterium strain lacking VirE2, e.g. W5000 (Dombek and Ream. J Bacteriol. 1997.1165–1173). Agrobacteria deficient for VirE2 are incapable of transferring T-DNA to a plant host. Thus the agrobacterium strain harboring the recombinant recA library plasmids can be evaluated by a quantitative tumorigenesis assay, (as described in Shurvington and Ream. J. Bacteriol. 1991. 173:5558–5563). Briefly, an appropriate plant substrate, such as potato tuber disks, or *Kalanchoe daigremontiana* leaves are infected with approximately $1 \times 10^7$ CFU of Agrobacterium. The disks or leaves are cultured for between either 3 or 4 weeks, respectively, and scored for tumor formation. Only agrobacterium encoding RecA protein which complements VirE2 function will form tumors in this assay.

VirE2 deficient agrobacteria carrying a selectable marker between T-DNA borders are transformed with recombinant RecA library members and incubated with target plant cells or explants in culture. After washing to remove the agrobacteria from co-culture, the plant cells or explants are subjected to culture under conditions appropriate for selection of the marker. Only if the evolved RecA molecule is capable of providing substituting for VirE2 will the selectable marker be transferred, generating resistant plant cells or explants.

Recombinase Transgenic Plants

While it is clear that agrobacteria lacking VirE2 functions are unable to transform host plants, it has been shown that VirE2 deficient agrobacteria can mediate transfer of a T-DNA strand if VirE2 is supplied in trans by the host plant cell. Other embodiments of the invention take advantage of this finding with an alternative to the above transformation and screening process. Transgenic plants or plant cells expressing the evolved recombinase constructs described above, can be generated by any one of several means, including but not exclusively, microinjection, electroporation and biolistics. Subsequently these can be used as the target for infection by a VirE2 deficient agrobacterium strain carrying a selectable marker between T-DNA borders. After infection, selection is carried out as described above.

Nuclear targeting of the transferred T-DNA is essential for transformation. Nuclear localization signals on both VirD2 and VirE2 are thought to help guide the T-DNA to the nucleus where it is integrated into a host plant chromosome. In some of the embodiments of the invention, a nuclear localization signal, derived from either VirE2 or another source, is added to the evolved recombinase molecule to enhance the transport of T-DNA to the plant cell nucleus

EXAMPLE

Arabidopsis Transgenic for VirE2 Complementary RecA

In another aspect of the present invention, evolved recA genes identified in the quantitative tumorigenesis assay of the first example above are used to produce transgenic plants which serve as the basis for homologous recombination experiments. Both VirD2 and VirE2 contain nuclear localization signals (NLS) that are involved in targeting T-DNA to the plant cell nuclei. While it is not certain that the VirE2 NLS are essential for transport of the T-DNA to the nucleus, they probably increase the efficiency of targeting. For example, the NLS of VirE2 is comprised of two amino acid sub-sequences rich in basic amino acids with the sequence NS1: KLRPEDRYVQTERYGRR (SEQ ID NO: 1); NS2: KRRYGGETEIKLKSK (SEQ ID NO: 2).

In the invention, to enhance the efficiency of T-DNA transport to the nucleus by an evolved RecA mediated process, NLS derived from VirE2, VirD2 or another source are added to the evolved recA genes identified above. Evolved recA DNAs encoding VirE2 complementary RecA proteins are then cloned between T-DNA borders on plasmids bearing a marker, for example: bar, (the bialaphos resistance gene of *Streptomyces hygroscopicus*) suitable for selection in transformed plants, e.g. pWBVec5, (Wang and Upadhyaya, Proc. Int. Symp. Biotech. 1998. 401–407). The plasmid is then introduced into agrobacteria and the agrobacteria used to infect *Arabidopsis thaliana* seedlings by the vacuum infiltration transformation procedure, (Bechtold et al. 1998. Methods Mol. Biol. 82:259–66).

In brief, *Arabidopsis thaliana* seeds are incubated at 4° C. for two days then transferred to growth chambers and grown at 24° C., 60–80% relative humidity, with a 16 hours light, 8 hours dark photoperiod for three weeks. Agrobacterium strains carrying an evolved recA plasmid are grown for two days in Luria Broth (LB). The cultures are spun down and the agrobacteria are resuspended in an equal volume of infiltration medium (2.2 g MS salts, 50 g sucrose, 1×B5 vitamins, 0.5 g MES, 0.044 μM benzylaminopurine, 200 μl Silwet L-77/1, pH 5.7). Arabidopsis plants are submerged for approximately 5 minutes in the bacterial suspension under a vacuum of 400 mm Hg. After quick release of the vacuum, the infiltrated plants are grown for an additional three weeks under plastic wrap. Seeds are harvested and resown. After germination, seedlings are treated with a 0.5% Basta solution. Transgenic plants expressing the bar gene, survive the herbicide treatment and are used for subsequent analysis.

RecCA/VirE2 Fusion Protiens

To gain additional functional specificity provided by VirE2 while taking advantage of the high frequency of homologous recombination conferred by RecA, some embodiments rely on fusion proteins comprising novel functional combinations of domains derived from VirE2 and RecA.

EXAMPLE

RecA/VirE2 Fusion Proteins

In some embodiments, a RecA/VirE2 fusion protein replaces or augments VirE2. RecA/VirE2 fusions can be developed either by any of a number of diversity generating procedures, e.g., shuffling, as described above, or by recombining functional domains in a rational design strategy. For example, in one embodiment, DNA shuffling involves combining fragments derived from various recA gene homologues with agrobacterial VirE2 genes in vitro. PCR is utilized to reconstitute recombinant DNA segments encoding RecA/VirE2 fusion proteins. Alternatively, disparate domains chosen for their putative or proven functional activity, can be selected from various RecA and VirE2 homologues and recombined by standard recombinant DNA techniques. For example, the RecA DNA binding motifs designated L1 and L2 and corresponding respectively to *E.coli* amino acid residues 157–164 and 195–209, are combined in the same fusion protein as the VirE2 NLS.

In either case, multiple RecA/VirE2 fusion proteins encoding DNA segments are produced. These DNA segments are optionally recombined and cloned into appropriate helper plasmids which are introduced into a VirE2 null agrobacterium strain. An agrobacterium strain harboring a RecA/VirE2 hybrid DNAs is assayed for VirE2 complementation by a quantitative tumorigenesis assay. Agrobacterium encoding RecA protein which complements VirE2 function form tumors as described above.

RecA activity is assayed by introducing the RecA/VirE2 plasmid into a disarmed agrobacterium strain lacking the oncogenic functions necessary for tumor formation. This agrobacterium strain is used to transform Arabidopsis plants which are evaluated for their ability to repair DNA by homologous recombination in response to mitomycin C exposure. Protoplasts are prepared from transgenic Arabidopsis leaves by standard plant culture methods. Briefly, cut leaves are digested with cellulase and pectinase (1–20 mg/ml, pH 5.6) at 22° C. for 16 hours in the dark. Protoplasts are then purified by filtration through steel sieves, (250 μM and 100 μM mesh width). After washing, protoplasts are resuspended in MaMg buffer (0.5 M mannitol, 15 mM MgCl2, 0.1% Mes, pH 5.7) to which mitomycin C is added at a concentration of 5–50 μg/ml. Survival in mitomycin C is dependent on the ability to efficiently repair damaged DNA by homologous recombination supplied by expression of a RecA/VirE2 fusion protein with RecA activity.

Production of Transgenic Organisims Using Evolved Recombinases

Numerous techniques exist for introducing exogenous DNA sequences into the genome of a host organism to produce a transgenic organism which has stably integrated the foreign DNA into its genome. In animals as well as in plants, these integration events are generally random in nature. Protocols for integrating exogenous DNA to a predetermined site in a host genome, rely on the selection or screening of very low frequency events. Many such protocols further require the presence of extensive regions of homology between the exogenous DNA and the desired insertion site. The present invention provides a means, generalizable to both prokaryotic and eukaryotic organisms, for integrating an exogenous DNA sequence into a predetermined site in a host genome. An exogenous DNA is introduced along with an evolved recombinase into a host cell of choice by any one of a number of methods, which include microinjection, electroporation, lipofection, and biolistics, as well as other techniques well-known in the art.

The evolved recombinase, which can be, but is not limited to, a RecA homologue, is used to mediate recombination between the exogenous DNA substrate and a predetermined site within the host genome with which the exogenous DNA shares a limited region of sequence similarity. The cells are then screened for the desired targeted integration event, and if desired, regenerated to produce a multicellular transgenic organism. A preferred embodiment of the present invention takes advantage of Agrobacterium mediated transformation to further refine targeting of plant and fungal genomes.

Production of Transgenic Plants by Homologous Recombination

RecA and RecA/VirE2 fusion proteins that mediate T-DNA transfer by homologous recombination with a predetermined target site in a plant chromosome have enormous potential in the derivation of improved plant hybrids. Agrobacterium expressing the modified recombinase proteins or RecA/VirE2 fusion proteins of the invention are useful in delivering exogenous DNA to specific sites in a plant host chromosome through the well established techniques of agrobacterium mediated transformation. T-DNA constructs bearing DNA sequences of interest and sharing regions of sequence similarity to a specific site in the target genome between T-DNA borders are produced by standard techniques for processing recombinant DNA. Regions of sequence similarity as small as a few hundred nucleotides have been shown to efficiently guide RecA mediated homologous recombination, although shorter regions have been shown to work, albeit with lower efficiency.

In the invention, RecA homologue or RecA/VirE2 fusion proteins substitute for or augment VirE2 function. A plasmid comprising the shuffled RecA homologue or fusion protein is transformed into an agrobacterium strain which is then used as a vector in the transformation of plant cells or explants. To obtain insertion of a transgene at a predetermined locus in a plant chromosome, a construct is designed which incorporates the exogenous DNA or altered DNA sequence of interest, between regions with sequence similarity to desired locus of insertion, between T-DNA borders. Minimally, the exogenous DNA sequences and the flanking regions of sequence similarity can be positioned adjacent to only a right T-DNA border. Such single T-DNA border constructs are capable of being excised by VirD proteins, bind VirD2 and VirE2, and are transferred as T-DNA to a host cell.

In an embodiment, the RecA homologue or RecA/VirE2 fusion protein is encoded by a helper plasmid which supplies vir function in trans to the exogenous DNA sequences which comprise the T-DNA. The plasmid containing the T-DNA, and the plasmid which encodes vir function, together comprise a binary vector system. Such binary vector systems provide for the efficient transformation of host plant cells, while permitting the production of T-DNA constructs unburdened by the difficulty of manipulating a 200 kilobase or larger plasmid. In a preferred embodiment, the RecA homologue or RecA/VirE2 fusion protein is encoded on the chromosome in an agrobacterium that is VirE2 deficient.

During infection by an agrobacterium strain described above, the T-DNA bearing the exogenous sequences is excised by VirD proteins. VirD2 bind the right T-DNA border and the T-DNA strand is unwound from the donor DNA duplex. Either prior to transfer of the T-DNA or after its transfer to the host plant cell, the T-DNA is coated with the shuffled RecA homologue or RecA/VirE2 fusion protein. In a preferred embodiment, a nuclear localization signal present on the RecA homologue or RecA/VirE2 fusion protein directs the transferred T-DNA to the plant cell nucleus. In the nucleus, a search for sequence similarity and alignment with the target site ensues, facilitated by the RecA homologue or fusion protein.

A specific case where the desired locus of insertion is an endogenous gene corresponding to the exogenous DNA sequences is described below. Insertion of exogenous DNA sequences into a site corresponding to the sequences' genomic locus is essential in the production of so-called "knock-out" transgenic organisms. Simultaneous inactivation of an endogenous gene and insertion of a selectable marker can be performed by homologously recombining a suitable construct with the genomic allele corresponding to the sequences of interest. A suitable construct typically consists of a selectable marker, such as an antibiotic resistance gene, driven by its own promoter, inserting into, and replacing a comparably sized region of, wild-type gene sequences. This results in the marker gene being flanked by regions of sequence similarity, several hundred base pairs to several kilobase pairs in length, to the endogenous allele. To introduce this construct into plant cells, this marker-flanking sequence cassette is then cloned between T-DNA borders, and transformed into an appropriate agrobacterium strain. For example, a strain with a helper plasmid comprising a RecA/VirE2 fusion protein as described above. The agrobacterium strain is then introduced under co-culture conditions into protoplasts or other cells or explants capable of regeneration. After selection with the appropriate antibiotic, resistant cells which have incorporated the marker into the endogenous allele of interest can be further characterized to insure that recombination mediated by the RecA/VirE2 fusion has occurred at the desired insertion site. Integration at the site of the endogenous gene, thus results in substitution of an interrupted and therefore inactivated gene, at the original locus.

EXAMPLE

Generation of Transgenic Arabidopsis by Homologous Recombination

In an embodiment of the present invention, an agrobacterium binary vector is constructed using a nptII selectable marker embedded in an Arabidopsis nitrate reductase (nia2) gene. Replacement of nia2 sequences with nptII interrupts the coding sequence of nia2, resulting in an inactivated allele of the gene. Inactivation of nia2 causes Arabidopsis to become resistant to the herbicide chlorate. The inactived nia2/nptII gene is cloned between T-DNA borders of a suitable plasmid and introduced into an appropriate Agrobacterium strain, e.g., the Agrobacterium strain of the first example above, carrying an evolved RecA plasmid. In another embodiment, the evolved RecA has a NLS. In a preferred embodiment, a RecA/VirE2 plasmid is used in place of the RecA plasmid.

The Agrobacterium strain is used to transform Arabidopsis by the vacuum infiltration method described previously, or by other comparable methods known in the art. Seeds are recovered and plated on medium containing Kanamycin to determine the total number of transformed plants. The transgenic plants germinated under Kanamycin selection are subjected to the herbicide chlorate to assess the frequency of insertion at the nia2 genomic locus. Alternatively, an Arabidopsis strain deficient in nitrate reductase can be transformed with a T-DNA containing a complementing fragment of a nitrate reductase gene. Plants in which the complementing nitrate reductase gene integrates via homologous recombination can be selected by growing the seedling on a medium cotaining nitrate as the sole source of nitrogen.

Alternatively, the parental Agrobacterium strain, lacking the RecA or RecA/VirE2 fusion constructs can be transformed with the inactivated nia2/nptII plasmid and used to infect the transgenic plants generated in the second example above. Seeds recovered are germinated in the presence of Kanamycin as described and subsequently subjected to chlorate to determine the frequency of targeted disruption at the nia2 locus.

various recombinases or homologues having recombinase activity can be substituted for RecA. All publications, patents, patent applications, or other documents cited in this application are incorporated by reference in their entirety for all purposes to the same extent as if each individual publication, patent, patent application, or other document were individually indicated to be incorporated by reference for all purposes.

SEQUENCE LISTING

```
<160> NUMBER OF SEQ ID NOS: 2

<210> SEQ ID NO 1
<211> LENGTH: 17
<212> TYPE: PRT
<213> ORGANISM: Agrobacterium tumefaciens

<400> SEQUENCE: 1

Lys Leu Arg Pro Glu Asp Arg Tyr Val Gln Thr Glu Arg Tyr Gly Arg
1               5                   10                  15

Arg

<210> SEQ ID NO 2
<211> LENGTH: 15
<212> TYPE: PRT
<213> ORGANISM: Agrobacterium tumefaciens

<400> SEQUENCE: 2

Lys Arg Arg Tyr Gly Gly Glu Thr Glu Ile Lys Leu Lys Ser Lys
1               5                   10                  15
```

Identification of Novel Gene Products Which Stimulate Homologous Recombination.

Another aspect of the present invention provides for the identification of novel proteins which influence the rate of homologous integration of transgenes in plants. Genes located on a T-DNA are maintained extrachromosomally and expressed in plant cells. Using a suitable screening or selection system, e.g., as described above, integration via homologous recombination can be monitored. In one approach, known bacterial and/or eukaryotic genes involved in DNA recombination and repair are assayed. Alternatively, a cDNA library of genes derived from *Saccharomyces cerevisiae, Aspergillus awamori* or *Aspergillus kluyveri* is assayed. These species are especially likely to yield genes which encode proteins which stimulate homolgous recombination. In *S. cerevisiae*, transformation frequently occurs by homologous recombination. In addition, Agrobacterium derived T-DNAs can integrate via homologous recombination in the latter two species (Gouka et al. 1999. Nature Biotechnology 17:598–601). Another approach is to screen a cDNA library constructed from eukaryotic cells or tissues undergoing meiosis. Such tissues are expected to express genes necessary for homologous recombination. Potential source tissues include plant flower components and animal gonadocytes.

While the foregoing invention has been described in some detail for purposes of clarity and understanding, it will be clear to one skilled in the art from a reading of this disclosure that various changes in form and detail can be made without departing from the true scope of the invention. For example,

What is claimed is:

1. A method of evolving a recombinase to complement an Agrobacterium virE2 gene, the method comprising:
   (a) providing a population of nucleic acids, wherein the population encodes a plurality of recombinase genes;
   (b) recombining or mutating the population of nucleic acids to generate a library of recombinant nucleic acid segments;
   (c) optionally repeating the recombining or mutating process of steps (a) and (b) one or more times; and
   (d) screening the library of recombinant nucleic acid segments, which recombinant nucleic acid segments comprise evolved recombinase genes, to identify at least one recombinant nucleic acid segment encoding an evolved recombinase, which evolved recombinase can substitute functionally for an Agrobacterium virE2 gene in plant transformation.

2. The method of claim 1, wherein step (b) comprises recombining and mutating the population of nucleic acid segments.

3. The method of claim 1, comprising recombining the population of nucleic acids by nucleic acid shuffling.

4. The method of claim 1, comprising providing the population of nucleic acids by enzymatic, chemical or mechanical cleavage.

5. The method of claim 4, wherein the recombining comprises:
   (i) providing a population of overlapping single stranded nucleic acids in vitro;
   (ii) annealing the overlapping population of single stranded nucleic acids to produce a population of partially overlapping double stranded nucleic acids;

(iii) extending the population of partially overlapping double-stranded nucleic acids with a polymerase; and (iv) repeating steps (i) through (iii) to produce a library of recombinant nucleic acid segments comprising evolved recombinase genes.

6. The method of claim 1, wherein the recombinase gene is recA.

7. The method of claim 1, wherein the recombinase gene comprises a eukaryotic recombinase gene.

8. The method of claim 1, wherein the recombinase gene is rad51 or dmc1.

9. The method of claim 1, wherein the population of nucleic acids comprises an Agrobacterium virulence gene.

10. The method of claim 9, wherein the population of nucleic acids comprises the virE2 gene.

11. The method of claim 1, the screening of step (d) comprising expressing the library of recombinant DNA segments, which recombinant DNA segments encode an evolved recombinase, in a VirE2 deficient agrobacterium.

12. The method of claim 1, the screening of step (d) comprising expressing the library of recombinant DNA segments, which recombinant DNA segments encode an evolved recombinase, in plant cells, which plant cells are transformed by a VirE2 deficient agrobacterium.

* * * * *